US00PP35669P2

(12) United States Plant Patent
Brown

(10) Patent No.: US PP35,669 P2
(45) Date of Patent: Feb. 27, 2024

(54) ***PULMONARIA* PLANT NAMED 'SILVER SCIMITAR'**

(50) Latin Name: ***Pulmonaria* hybrid**
Varietal Denomination: Silver Scimitar

(71) Applicant: Terra Nova Nurseries, Inc., Canby, OR (US)

(72) Inventor: Kenneth Brown, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/116,037

(22) Filed: Mar. 1, 2023

(51) Int. Cl.
*A01H 5/02* (2018.01)
*A01H 6/00* (2018.01)

(52) U.S. Cl.
USPC ..... Plt./473
CPC ..... *A01H 6/00* (2018.05)

(58) Field of Classification Search
USPC ..... Plt./473
CPC ..... A01H 5/02
See application file for complete search history.

(56) References Cited

PUBLICATIONS https://www.pennlive.com/gardening/2023/01/the-best-new-perennial-flowers-of-2023-george-weigel.html; Jan. 19, 2023; 1 page.*
https://www.preen.com/learn/lawn-garden-tips/plants-trees-shrubs/perennials/seven-of-the-best-new-perennial-flowers-of-2023/; 2023; 4 pages.*
https://www.bfgsupply.com/media/6179/2022-2023-terra-nova-product-program.pdf; 2022-2023; 11 pages.*
https://www.canr.msu.edu/hrt/our_gardens/Visit/Amien-and-Florence-Carter-Trial-Garden/2022%20Trial%20Booklet; 2022; 41 pages.*
https://www.ditoplant.nl/?p=pagina&s=30&lang=en; Jul. 26, 2023; 2 pages.*

* cited by examiner

*Primary Examiner* — Kent L Bell
(74) *Attorney, Agent, or Firm* — The Webb Law Firm

(57) ABSTRACT

A new and distinct *Pulmonaria* plant characterized by its large, multicolored flowers, mature silver foliage without prominent spotting, high vigor, and powdery mildew tolerance.

2 Drawing Sheets

Botanical classification: *Pulmonaria* hybrid.
Varietal denomination: 'Silver Scimitar'.

BACKGROUND OF THE NEW PLANT

The present invention comprises a new and distinct *Pulmonaria* plant, of the family Boraginaceae, having the varietal name 'Silver Scimitar'. The new variety originated as an open-pollinated seedling of unknown parentage, as it was discovered in a cultivated garden surrounded by unnamed proprietary clones of mostly hybrids of *P. saccharata* x *P. longifolia* in Canby, Oregon. Therefore, the exact parentage is unknown. Pollination likely ocurred in early spring of 2017. The instant plant most closely resembles the *P. longifolia* species. Seedlings were grown and evaluated and 'Silver Scimitar' was selected for its very large, silver leaves, powdery mildew tolerance, and large habit.

When compared to its possible parent plants of the cultivated garden, the new variety has a larger habit, bright silver foliage color, and larger, multicolored flowers. When compared to *Pulmonaria* plant named 'Raspberry Splash' (U.S. Plant Pat. No. 12,138), the new variety has a larger habit and larger, multicolored flowers rather than raspberry pink colored flowers.

The new variety has only been reproduced by asexual propagation (division and tissue culture) beginning in June of 2018 in Canby, Oregon. Each of the progeny exhibits identical characteristics to the original plant. Asexual propagation by division and tissue culture using standard micropropagation techniques with terminal and lateral shoots performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Pulmonaria* plants known to the breeder, the new variety is characterized by the following:

1. Multicolored flowers in large displays;
2. Larger flower size;
3. Mature foliage without prominent spotting;
4. Powdery mildew tolerance; and
5. High vigor.

DESCRIPTION OF THE DRAWINGS

The accompanying photographic drawings illustrate the new variety at approximately 1 year of age, with the colors being as nearly true as possible with color illustrations of this type.

DETAILED BOTANICAL DESCRIPTION

Figure 1:
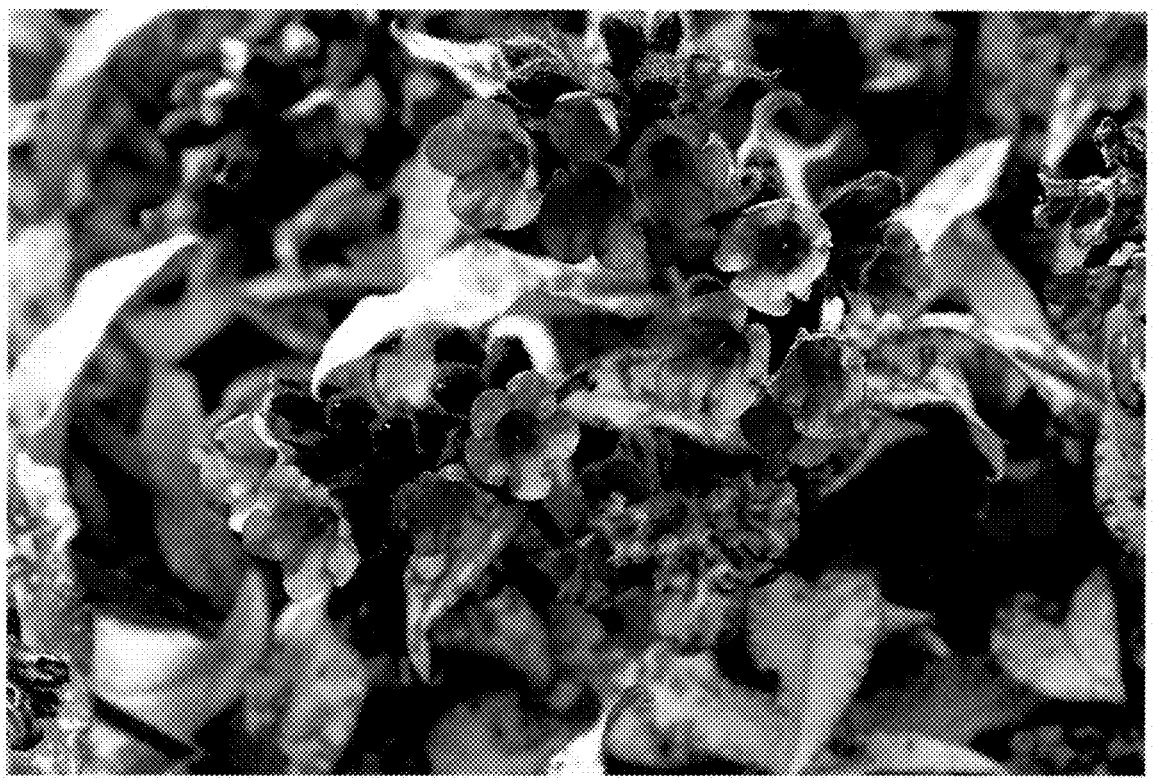
FIG. 1 illustrates a close-up of view of the flowers of the new variety in Canby, Oregon in May.
Figure 2:
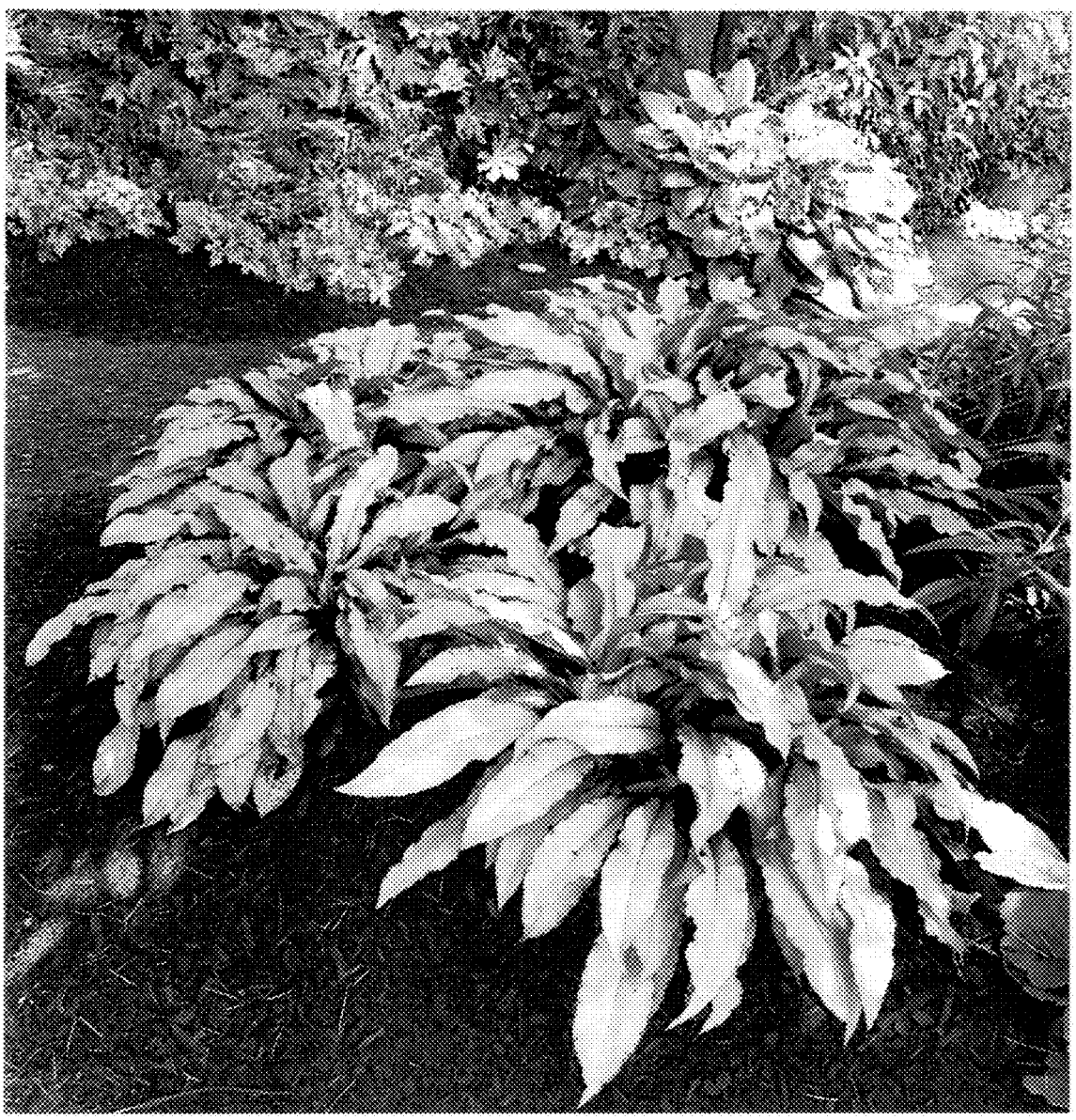
FIG. 2 illustrates the mature foliage of the new variety in Canby, Oregon in September.

The following is a detailed description of the new variety based on observations of 14-month-old plants grown under field conditions in full sun in Canby, Oregon (USDA Zone 8). Temperatures range from a high of 35° C. in August to a low of 0° C. in January. Normal rainfall in Canby, Oregon is around 1 m per year. Color references are based on the 2007 R.H.S. Colour Chart of The Royal Horticultural Society of London, 5th Edition.

Plant:

*Type.*—Herbaceous perennial.

*Hardiness.*—USDA Zones 4 to 9.

*Spring size.*—45.0 cm wide and 36.0 cm tall.

*Summer size.*—55.0 cm wide and 28.0 cm tall.

*Form.*—Clumping.

*Vigor.*—High.

*Root description.*—Thickened and fleshy.

Foliage:

*Type.*—Simple.

*Leaf arrangement.*—Rosette.

*Shape.*—Lanceolate to ovate.

*Length.*—To 30.0 cm.

*Width.*—6.0 cm at the widest point.

*Margin.*—Entire.

*Apex.*—Acuminate.

*Base.*—Attenuate.

*Leaf texture* (*both surfaces*).—Scabrous and sparingly glandular.

*Upper surface color.*—RHS 190D to 190C at the base.

*Lower surface color.*—RHS 192C.

*Venation.*—Pinnate.

*Petiole length.*—10.0 to 19.0 cm.

*Petiole diameter.*—5.0 mm.

*Petiole texture.*—Scabrous and sparingly glandular.

*Petiole color.*—Mostly RHS 71B, except near the blade where the coloration is RHS 194A.

*Cauline leaves.*—Presence: Found only in the spring on the flowering stems. After seed is produced, these stems die out. Type: Simple. Arrangement: Alternate. Shape: Oblanceolate to ovate. Length: Variable, 3.0 to 5.0 cm. Width: To 17.0 mm. Margin: Entire. Apex: Acuminate. Base: Clasping, sessile. Texture: Hispid. Venation: Pinnate. Upper surface color: RHS 137B with spots of RHS 192D. Lower suface color: Closest to RHS 192A.

Flowers:

*Bud.*—Length: 12.0 mm, with 4.5 mm extruding from the calyx. Width: 3.0 mm. Shape: Ovoid. Color: RHS 71B.

*Type.*—Actinomorphic.

*Inflorescence type.*—Terminal, forked cymes.

*Flower number per cyme.*—From 12 to 40.

*Inflorescence.*—Length: 8.0 cm. Width: 12.0 cm. Longevity: Individual flowers last from 5-7 days on the plant.

*Number of inflorescences in first spring flush.*—About 80.

*Bloom period.*—March to May in Canby, Oregon.

*Fragrance.*—None.

*Peduncle.*—Length: 16.0 cm. Width: 4.0 mm. Texture: Hispid. Color: Closest to RHS 147B.

*Pedicel.*—Length: 2.0 to 10.0 mm. Texture: Hispid. Color: RHS 200B. Diameter: 0.75 mm.

*Corolla.*—Shape: Funnelform. Arrangement: 5 fused petals with rounded lobes. Depth: 2.0 cm. Width: 2.0 cm. Tube size: 9.0 mm long and 2.0 mm wide. Lobes: Depth: 4.0 mm. Width: 6.0 mm. Margins: Entire. Tips: Obtuse. Texture: Satiny (both surfaces). Color (young flowers): Inside color of RHS 51A, the outside color is RHS 70A on the cup, RHS 71A on the top half of the tube, and RHS NN155A on the bottom half. Color (mature flowers): Outside color shift to RHS 91A with RHS 72B stripes located between the fused petals.

*Calyx* (*sepals*).—Arrangement: 5 fused sepals. Shape: Tubular campanulate, parted ¼ to the base. Size: 1.3 cm deep and 6.0 mm wide. Apex: Acute. Margin: Entire. Texture: Hispid. Color: Outside color closest to RHS N187A, inside color of RHS 147B.

*Pistil.*—1; 12.0 mm long.

*Ovary.*—1.0 mm deep and 1.5 mm wide; RHS 146A.

*Style.*—Pin type, exerted from the corolla tube; 14.0 mm long; RHS 155B.

*Stigma.*—RHS N200A.

*Stamen.*—5 anthers in number, attached to and inserted in the top of the corolla tube; RHS 203B; 2.0 mm in length.

*Pollen.*—Moderate; RHS NN155A.

Seeds:

*Type.*—4 smooth nutlets.

*Color.*—RHS 202A and shiny.

*Fertility.*—Low.

Pests/diseases: Tolerant to powdery mildew. No other unusual resistance or susceptibility to pests or diseases noted to date.

I claim:

1. A new and distinct variety of *Pulmonaria* plant named 'Silver Scimitar', substantially as illustrated and described herein.

* * * * *